United States Patent [19]

Ogawa

[11] Patent Number: 4,522,921
[45] Date of Patent: Jun. 11, 1985

[54] SAMPLE DELIVERING METHOD FOR USE IN AUTOMATIC CHEMICAL ANALYSIS

[75] Inventor: Yuji Ogawa, Kamifukuoka, Japan

[73] Assignee: Olympus Optical Co., Ltd., Tokyo, Japan

[21] Appl. No.: 448,077

[22] Filed: Dec. 9, 1982

[30] Foreign Application Priority Data

Dec. 11, 1981 [JP] Japan ................................ 56-198357

[51] Int. Cl.³ ............................................ G01N 35/06
[52] U.S. Cl. ...................................... 436/47; 422/64; 422/65; 422/67; 436/45
[58] Field of Search ..................... 141/1, 83, 138, 139; 422/63-65, 67; 436/43-49, 54; 198/358

[56] References Cited

U.S. PATENT DOCUMENTS 3,578,412  5/1971  Martin .............................. 436/47 X
3,854,879  12/1974 Figueroa et al. ...................... 436/47
3,869,252  3/1975  Hauq ................................ 422/65
4,004,620  1/1977  Rosen ............................ 141/138 X
4,042,338  8/1977  Huber ................................ 422/64

FOREIGN PATENT DOCUMENTS 1321754  6/1973  United Kingdom .................. 422/65

Primary Examiner—Barry S. Richman
Assistant Examiner—Michael S. Gzybowski
Attorney, Agent, or Firm—Parkhurst & Oliff

[57] ABSTRACT

A sample delivering method for use in a multi-channel multi-item automatic chemical analyzer having a plurality of reaction lines corresponding to the test-items and a sample supplying line. A sample delivering region is determined in the reaction lines and the sample supplying line, and vacant reaction tubes in the sample delivering region are detected. Samples in the sample delivering region are delivered into the vacant reaction tubes which correspond to the test-items required for the samples. Therefore, it is possible to reduce the number of reaction tubes to be used in an analysis, and thus the through-put of the analyzer can be improved to a great extent as compared with a conventional automatic chemical analyzer.

8 Claims, 4 Drawing Figures

FIG_3

SAMPLE DELIVERING METHOD FOR USE IN AUTOMATIC CHEMICAL ANALYSIS

BACKGROUND OF THE INVENTION

The present invention relates to a sample delivering method for use in an automatic chemical analysis, particularly in a multi-channel multi-item automatic chemical analyzer.

Presently, most multi-item chemical analyzers can perform many different analyses for test-items by using a plurality of channels arranged to improve the test-item processing ability per unit hour, i.e., the through-put. However, when using these multi-channel multi-item automatic chemical analyzers, it is very rare for all test-items to be performed for each sample. Therefore, in the actual analysis many reaction tubes are not used.

FIG. 1 is a schematic view showing one embodiment of a conventional multi-channel automatic chemical analyzer. In FIG. 1, a plurality of reaction tubes 2 are arranged on a turntable 1 which rotates in a clockwise direction. The reaction tubes 2 are arranged along four channel reaction lines concentrically with respect to a center of the turntable 1. The respective reaction lines are denoted by numerals 3, 4, 5, 6 from outer to inner lines. The first three of these correspond to test-items $\alpha$, $\beta$, $\gamma$, respectively, while the last correspond to an undecided, i.e., variable, test. A plurality of sample tubes 7 are arranged along a sample line situated beside the turntable 1 and can move leftward as shown by an arrow. The sample tubes 7 are moved one step at a time in synchronism with the turntable 1. Starting from the tube situated at the delivering position X the sample tubes have been labeled A, B, C, D, respectively, and the corresponding reaction tube series are denoted by a, b, c, d, respectively. Therefore, relevant sample tubes A, B, C, D correspond to relevant reaction tube series a, b, c, d at the delivering position X. Moreover, a suitable delivering mechanism is arranged at the delivering position X to supply a sample contained in the sample tube into the reaction tubes. In this embodiment, the delivering mechanism functions to supply the sample at the delivering position X to first, second and third reaction lines 3, 4 and 5. It should be noted that the sample is not supplied to the fourth reaction line 6 by this delivering mechanism because the test-item for the reaction line 6 is undecided.

In the conventional multi-channel automatic chemical analyzer mentioned above, the sample is selectively delivered into the reaction tubes in accordance with test-items to be performed for the relevant sample. Now, for illustration it is assumed that the test-item $\alpha$ is to be performed for the samples A, B, C and D, the test-item $\beta$ is to be effected for the samples A and C, and the test-item $\gamma$ is to be effected for the samples B and C. The sample A then is delivered into the reaction lines 3 and 4 of the reaction tube series a, and then the sample B is delivered into the reaction lines 3 and 5 of the reaction tube series b after shifting the sample tube 7 and the turntable 1 by one step. Similarly the sample C is delivered into the reaction lines 3, 5 of the reaction tube series c, and the sample D is delivered into the reaction line 3 of the reaction tube series. Therefore if the step period is assumed to be T, the processing efficiency is 4/T.

However, in the conventional delivering method mentioned above, no analysis is performed for the reaction tubes in the reaction line 6 and thus the reaction tubes remain vacant. Moreover, even if a new test-item is selected for the reaction line 6, only very rarely will all the test-items be performed for each sample, and thus the drawback remains that many vacant reaction tubes which are not used for the analysis remain on the turntable.

SUMMARY OF THE INVENTION

The object of the present invention is to eliminate the drawbacks mentioned above and to provide a sample delivering method which improves the through-put of a multi-channel automatic chemical analyzer by reducing the number of vacant reaction tubes which are not used for analysis.

According to the invention, a sample delivering method for use in a multi-channel multi-item automatic chemical analyzer having a plurality of reaction lines, each being pre-set to perform given test-items, at least one sample supplying line, and a sample delivery means for delivering successive samples fed along the sample supplying line into at least one reaction tube in at least one reaction line, comprises the consecutive steps of:

setting a sample delivering region in said reaction lines and sample supplying line;

delivering a sample into at least one reaction tube selected from the reaction tubes in said sample delivering region, which reaction tube corresponds to a required test-item;

detecting whether any vacant reaction tubes are still present among the reaction tubes situated in said sample delivering region;

moving the samples along the sample supplying line by one step; and delivering a sample which is newly fed into the sample delivering region into at least one vacant reaction tube in the sample delivering region, if the relevant vacant reaction tube belongs to a test-item to be performed on the relevant sample.

DESCRIPTION OF THE PREFERRED EMBODIMENTS

Figure 1:
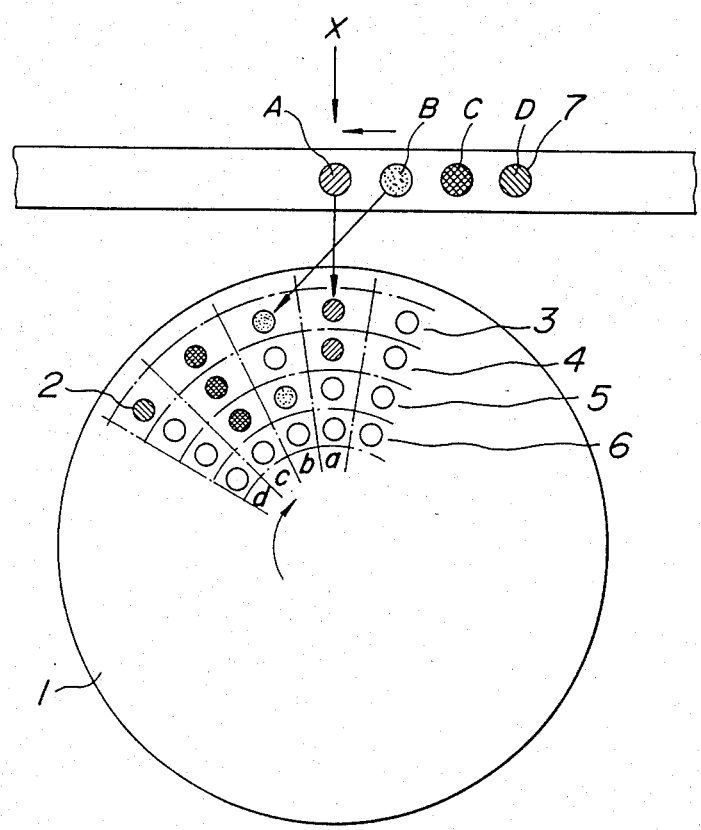
FIG. 1 is a schematic view showing one embodiment of a conventional multi-channel automatic chemical analyzer.
Figure 2:
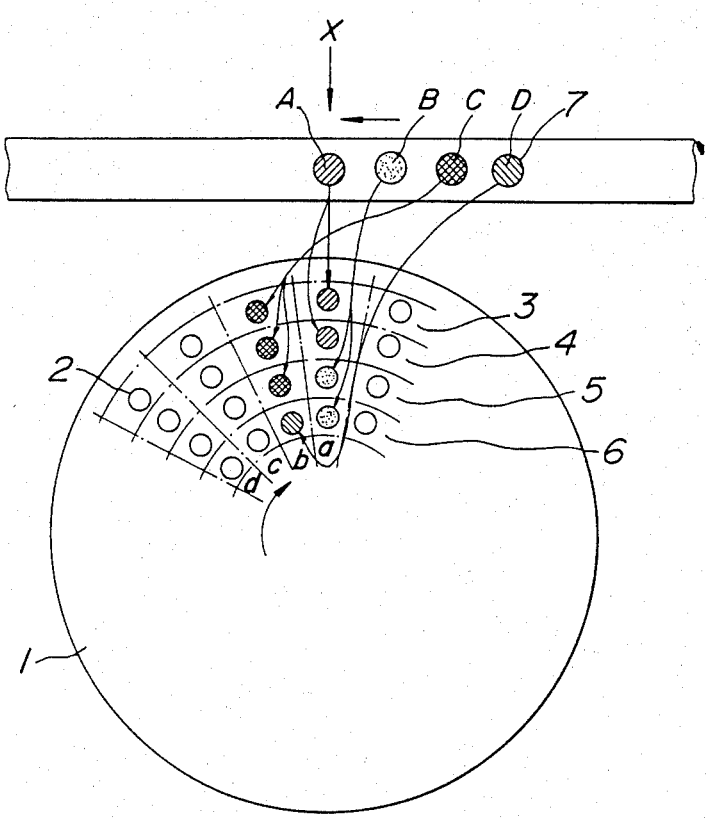
FIG. 2 is a schematic view illustrating one embodiment of a sample delivering method for use in a multi-channel chemical analyzer according to the invention.

FIG. 2 is a schematic view showing one embodiment of a sample delivering method for use in a multi-channel automatic chemical analyzer according to the invention. Items in FIG. 2 similar to those shown in FIG. 1 are denoted by the same reference numerals used in FIG. 1. In addition, in the embodiment shown in FIG. 2, the test-item $\alpha$ is performed on both the fourth reaction line 6 and the first reaction line 3. At first, a sample A is delivered into a reaction tube series a at a delivering position X. In this case, since the test-items $\alpha$ and $\beta$ are to be performed for the sample A, the sample A is delivered into the reaction lines 3 and 4 (which correspond to the test-items α and β) of the reaction line series a by means of a delivering mechanism not shown. Next, this delivering operation is stored in a central processing unit (hereinafter abbreviated as CPU). The CPU functions to detect vacant reaction tubes in the reaction tube series a and to deliver the next sample B into the vacant reaction tubes if the test-items to be effected for the sample B are identical with those of the vacant reaction tubes. In this example, since the reaction lines 5 and 6 of the reaction tube series a are vacant and the test-items of the next sample B are identical with those of the vacant reaction tubes, it is possible to deliver the sample B into the vacant reaction tubes in the series a. Therefore, while the sample tubes 7 are moved by one step, the turntable 1 is kept stationary, and the sample B is delivered into the reaction tubes situated on the reaction lines 5 and 6.

After the delivery for all the reaction tubes of both the reaction tube series a is ended, the turntable 1 and the sample tube 7 are moved by one step so as to deliver the sample C into the reaction tubes on the reaction lines 3, 4 and 5 of the reaction tube series b (assuming the test-items α, β and γ are to be effected for the sample C). In the reaction tube series b, the only vacant reaction tube is on the reaction line 6. Assuming the test-item of the next sample D is identical with that of the reaction line 6, i.e., only the test-item α is to be performed for the sample D, the reaction tubes 7 are moved by one step, while the turntable 1 is kept stationary, and the sample D is delivered into the reaction tube on the reaction line 6 of the reaction tube series b.

If all the test-items are to be performed for all the samples, the through-put of the method according to the invention is substantially same as that of the conventional method, but, as this is a very rare situation, usually many vacant reaction tubes which are not used for the analysis remain on the turntable in the known method. Therefore, if the sample delivering method according to the present invention is used for the multi-channel automatic chemical analyzer, the through-put is improved to a great extent. In order to deliver as many samples into one reaction tube series as possible, it is preferable to set the test-items to be frequently used in a plurality reaction lines. Especially when the whole reaction is unused, if the corresponding unused reaction line is reset to a frequently used test-item it is possible to further improve the through-put. In this manner, since the same test-item is effected in more than one channel, the through-put is improved materially. Further, since the sample is delivered into a plurality of reaction tubes at the same time, it is possible to make the amount of the sample used small and to make the sample delivering period long. Furthermore, if one reaction line is damaged, it is possible to use the other reaction lines as substitutes.

Figure 3:
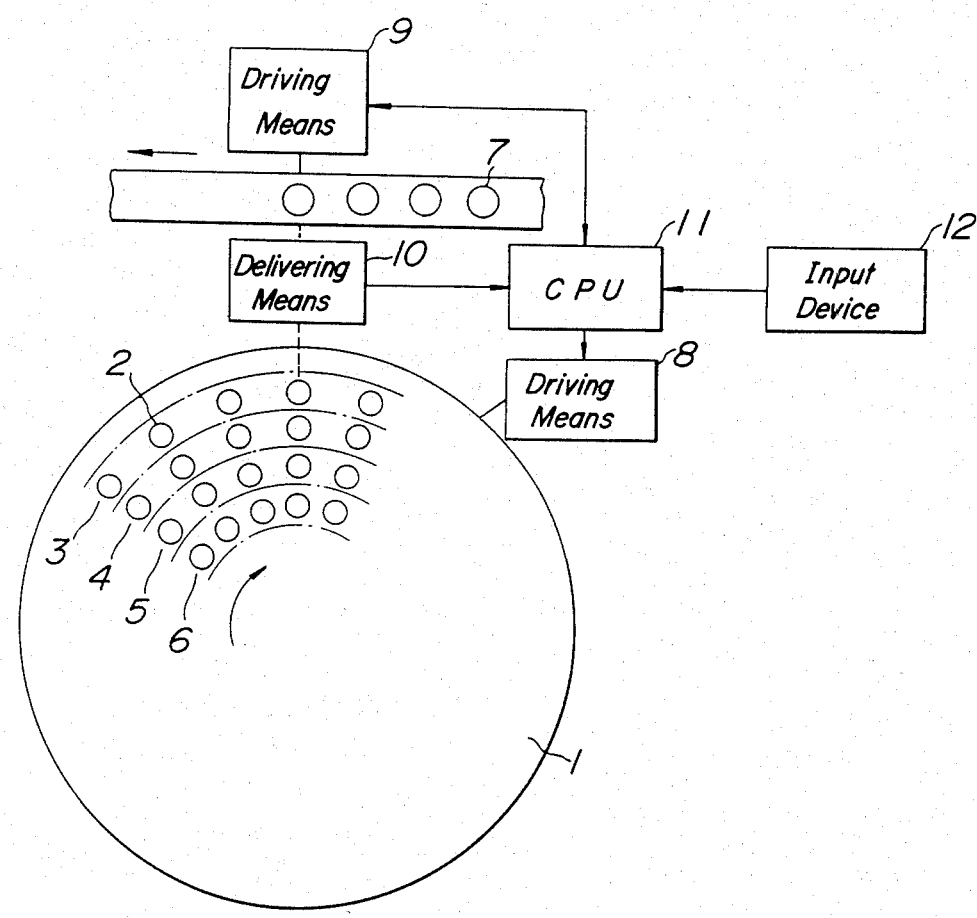
FIG. 3 is a block diagram depicting a control means for the multi-channel automatic chemical analyzer shown in FIG. 2.

FIG. 3 is a block diagram showing a control means for the multi-channel automatic chemical analyzer shown in FIG. 2. As shown in FIG. 3, a reaction tube driving means 8 for driving the turntable 1, a sample driving means 9 for driving the sample tubes 7 and a sample delivering means 10 for delivering the sample contained in the sample tubes 7 into the reaction tubes 2 are controlled by a CPU 11. The test-items to be performed for the respective samples are supplied by an input device 12 to the CPU 11. Further, the sample delivering means 10 functions to deliver the sample into the reaction tube 2 under the control of the CPU 11, and to supply the delivering information to the CPU 11.

After detecting the completion of a delivering operation, the test-items of the reaction tubes into which samples have not been delivered yet are compared with those of the next sample to be analyzed so as to detect the correlation therebetween. If it is possible to perform the sample delivery for the next sample, the sample tubes 7 are moved by one step while the reaction tube driving means 8 is kept stationery, and the sample is delivered to the appropriate reaction tubes 2. If it is not possible properly to deliver the sample into the remaining vacant tubes, both the turntable 1 and sample tubes 7 are moved by one step and normal sample delivery is performed.

Figure 4:
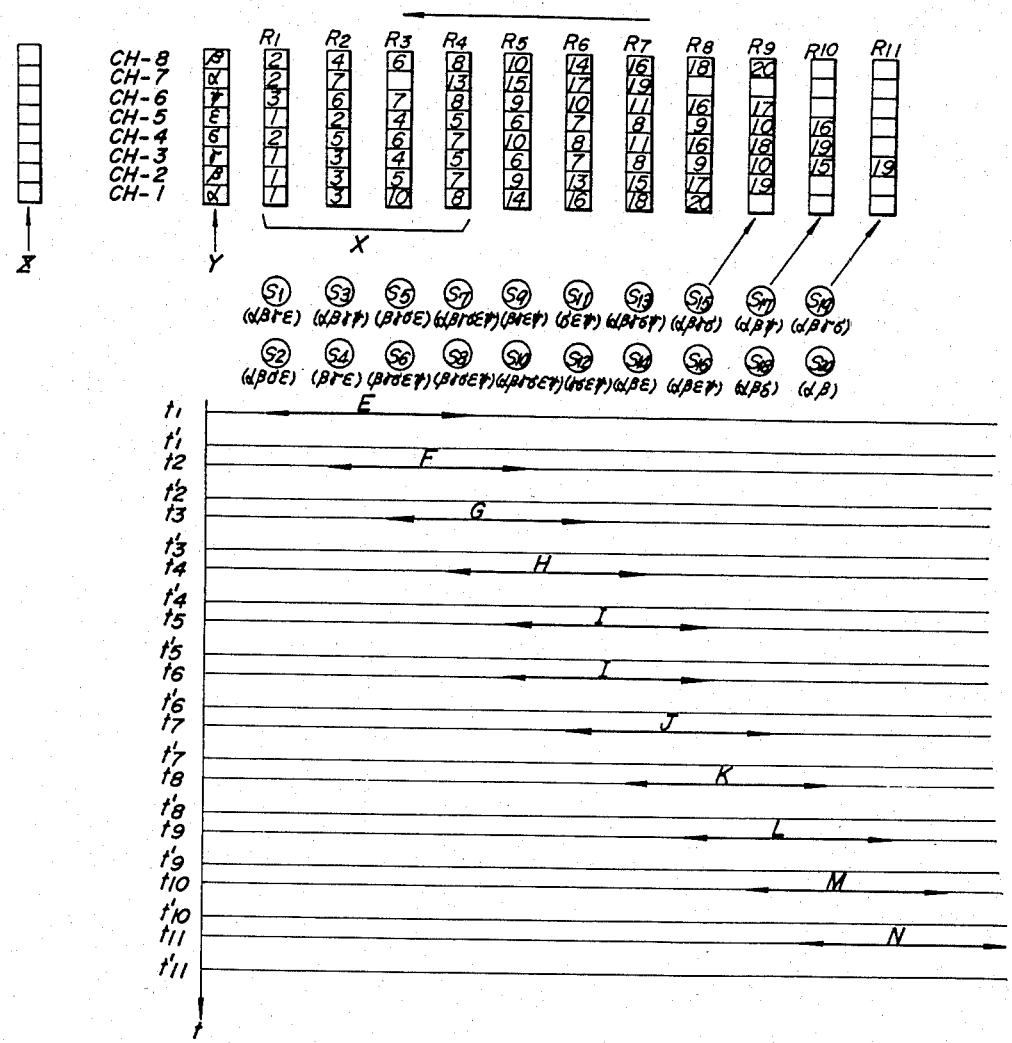
FIG. 4 is a schematic view showing another embodiment of the sample delivering method for use in a multi-channel chemical analyzer according to the invention.

FIG. 4 is a schematic view showing another embodiment of the sample delivering method for use in the multi-channel chemical analyzer according to the invention. In this embodiment, it is assumed that the test-items α, β, γ, δ, ε, ψ, α, β are effected in eight channels CH1 to CH8, respectively, and that reaction tube series $R_1$, $R_2$, $R_3$, ... which move to the left intermittently with a constant period, as shown in FIG. 4. Moreover, two sample supplying lines are arranged in parallel with each reaction channel. In FIG. 4, the samples on the sample supplying lines are denoted by numerals $S_1$, $S_2$, ..., and the required test-items for each sample are described under each samples in parentheses. For example, the test-items for the sample $S_1$ are α, β, γ and ε. In this embodiment, a sample delivering region X is determined as four reaction tube series (in FIG. 4, $R_1$ to $R_4$), and thus four sample delivery means are arranged to deliver the eight samples which correspond to the sample delivering region X (in FIG. 4, $S_1$ to $S_8$) into the four reaction tube series $R_1$ to $R_4$. The delivering operation for the sample delivering region X is performed during a period $\Delta T$. These sample delivery means also have a washing means to prevent a contamination between respective samples. Furthermore, in FIG. 4, number 1, 2, 3, which correspond to the thus delivered sample $S_1$, $S_2$, $S_3$, ... is shown in the reaction tubes on the reaction tube series. After delivering the samples into the reaction tubes, a reagent is delivered into the respective reaction tubes at a reagent supplying position Y, and then photometry is performed at a photometering position Z.

In this embodiment, both the reaction lines and the sample supplying lines move synchronously under the control of the CPU as shown in FIG. 3, and two sample supplying lines are provided to improve the through-put. These reaction lines and sample supplying lines are moved in such a manner that two samples on the sample supplying line correspond to one reaction tube series (for example, the samples $S_1$ and $S_2$ correspond to the reaction tube series $R_1$). In this embodiment, the sample is delivered into the reaction tube at the sample delivering region X, and then the vacant reaction tubes in this reaction tube series are detected and the next sample is delivered into these vacant reaction tubes if the test-items of these vacant reaction tubes match those of the next sample. Then, the desired reagent is delivered into the reaction tubes at the reagent supplying position Y situated in a downstream position of the reaction line, and the photometry is performed for the reaction tube series at the photometering position Z.

The delivering operation of the multi-channel automatic chemical analyzer mentioned above will now be explained with reference to FIG. 4.

The sample delivery starts with a sample group E consisting of the samples $S_1$ to $S_8$ at a time $t_1$. At first, since all the reaction tubes of the reaction tube series $R_1$ are vacant, all the test-items for the sample $S_1$ are satisfied by the series $R_1$ and thus the sample $S_1$ is delivered into the reaction tubes in the series $R_1$ corresponding to the required test-items. Then, the test-items of the next sample $S_2$ are compared with those of the vacant reaction tubes in the series $R_1$. In this embodiment, the test item $\epsilon$ is to be effected for both samples $S_1$ and $S_2$ and thus the sample $S_2$ is delivered into the corresponding reaction tube of the next reaction tube series $R_2$, i.e., channel-5, after delivering the sample $S_2$ into the reaction tubes in the series $R_1$ to which the test-items $\alpha$, $\beta$, $\gamma$ correspond. In this situation, since the channel-6 of the series $R_1$ remains vacant, it is determined whether the test-item $\psi$ corresponding to the channel-6 is required in the other samples $S_3$ to $S_8$ of the sample group E. In this example, the sample $S_3$ requires the test-item $\psi$, and thus the sample $S_3$ is delivered into the reaction tube in the series $R_1$. As described above, the delivering operation of the samples $S_1$, $S_2$ into the reaction tube series $R_1$ is ended, and then the reaction line and the sample supplying line are moved by one step at a time $t_1'$ ($t_1' = t_1 + \Delta t$) so that the new sample group F consisting of the samples $S_3$ to $S_{10}$ and the reaction tube series $R_5$ come into the sample delivering region X.

Next, at a time $t_2$, the samples $S_3$ to $S_6$ are delivered into the reaction tubes in the series $R_2$. In the example, all the test-items required for samples $S_3$ and $S_4$ can be performed in the vacant reaction tubes in the series $R_2$ and $R_3$, because the test-items of the samples $S_3$ and $S_4$ are $\alpha$, $\beta$, $\gamma$, $\psi$ and $\beta$, $\gamma$, $\epsilon$, respectively. Moreover, since the channels 6 ad 7 of the series $R_2$ remain vacant, the samples $S_6$ and $S_7$ (which require the corresponding test-items $\alpha$ and $\psi$) are delivered into the reaction tubes of the series $R_2$ corresponding to the channels 6 and 7, respectively. After that, at a time $t_2'$ ($t_2' = t_2 + \Delta t$), the reaction tube series $R_2$ and the samples $S_3$, $S_4$ leave the sample delivering region X, and the new sample group G reaches the region X.

Then, at a time $t_3$, the sample delivery for the new set of samples is effected. In the sample group G, the test-item $\alpha$ is required only for the samples $S_7$ and $S_{10}$ and they are already delivered into the channel-7 of the reaction tube series $R_2$ and the channel-1 of the series, respectively. Therefore, channel-7 (test-item $\alpha$) of the reaction tube series $R_3$ is left vacant. On the other hand, all the test-items of the samples $S_5$ and $S_6$ can be carried out by the reaction tube series $R_3$ to $R_6$ of the group G. In this case, even though a vacant reaction reaction tube remains in the series $R_3$, the reaction tube series $R_3$ and the samples $S_5$, $S_6$ leave the sample delivering region X at a time $t_3'$ ($t_3' = t_3 + \Delta t$) when the sample delivery for the samples $S_5$ and $S_6$ is finished. In the same manner, for the sample group H, the sample delivery for the samples $S_7$ and $S_8$ is finished during a period $t_4$ to $t_4'$ ($t_4' = t_4 + \Delta t$), the reaction tube series $R_4$ and the samples $S_7$, $S_8$ leave the sample delivering region X at a time $t_4'$.

At a time $t_5$, the sample delivery for the sample group I is started. In this case, since no vacant reaction tube remains for the test-items $\gamma$ and $\epsilon$ of the sample $S_{10}$ in the group I, the samples $S_9$ and $S_{10}$ cannot leave the sample delivering region X. Therefore, only the reaction line is moved by one step while the sample supplying line 13 is kept stationary. Then, at a time $t_6$, the test-items $\gamma$ and $\epsilon$ of the samples $S_{10}$ can be performed in the channels 3 and 5 of the reaction tube series $R_9$.

After that, for the sample groups J to N, since no vacant reaction tubes occur in the respective series, the reaction line and the sample supplying line are moved by one step immediately after the sample delivery for the samples is ended. As mentioned previously, the reagent is delivered into the respective reaction tube series $R_1$ to $R_{11}$ successively at the position Y situated at a downstream position along the reaction line, and, at the position Z, a predetermined photometry is performed. In this photometry, the photometries for the respective test-items are performed at the same time.

In the example, looking at the samples $S_1$ to $S_{10}$ will show that only the sample $S_2$ does not require the test-item $\gamma$, and thus the measuring frequency of $\gamma$ is very high. Therefore, it is preferable to arrange a plurality of reaction lines for the test-item $\gamma$ so as to improve the through-put. As for the test-item $\alpha$, two reaction lines are arranged in this embodiment, but are not effectively used. Therefore, in the example mentioned above, if the test-item $\gamma$ is exchanged with the test-item $\alpha$, it is possible to improve the through-put effectively.

As is clearly understood from the above explanation, according to the sample delivering method, since the sample delivery is performed for vacant reaction tubes corresponding to the test-items, it is possible to reduce the number of vacant reaction tubes, and thus it is possible to improve the through-put of the analyzer to a great extent.

The present invention is not limited to the embodiments mentioned above, but various modifications and alterations are possible. For example, the traveling direction of the sample tubes or the order of arrangement of the sample tubes can be changed at random in accordance with the position of the vacant reaction tubes, and thus it is possible to improve the through-put much more.

What is claimed is:

1. A sample delivering method for use in a multi-channel multi-item automatic chemical analyzer having a plurality of reaction lines comprised of reaction tubes, each line being previously set to perform given test-items, at least one sample supplying line carrying sample tubes containing successive samples to be analyzed, and a sample delivery means for delivering successive samples fed along the sample supplying line into at least one reaction tube in at least one reaction line, comprising the consecutive steps of:

setting a sample delivering region in said reaction lines and sample supplying line by selecting portions thereof to which and from which samples will be delivered;

delivering a portion of a sample into at least one reaction tube selected from the reaction tubes in said sample delivering region, which reaction tube corresponds to a test-item required for the sample;

detecting whether any vacant reaction tubes are present among the reaction tubes situated in said sample delivering region after said delivery;

moving the samples along the sample supplying line by one step to bring a new sample into said sample delivering region;

if vacant reaction tubes are detected, determining if any of them correspond to test-items required for said new sample; and, if any do so correspond, delivering a portion of the new sample into at least one said vacant reaction tube which so corresponds.

2. A sample delivering method according to claim 1, wherein the method further comprises the steps of moving the reaction tubes from said sample delivering region when no vacant reaction tubes are detected in said sample delivering region; and moving new reaction tubes into said sample supplying region, while the sample is retained in the sample supplying region.

3. A sample delivering method according to claim 1, wherein the number of the samples present in said sample supplying region equals the number of the reaction tubes existent in the sample supplying region.

4. A method according to claim 1, wherein said sample delivering region has a length measured along the sample supplying line such that a plurality of samples are existent in the sample delivering region at one time.

5. A sample delivering method according to claim 4, wherein a plurality of reaction lines are set to perform a test-item to be effected frequently.

6. A sample delivering method according to claim 1, wherein said sample delivering region has a length measured along the sample supplying line such that only a single sample is existent in the sample delivering region at one time.

7. A sample delivering method according to claim 6, wherein said sample delivering region has a length measured along the reaction lines such that only one reaction tube in each reaction line is present in the sample delivering region at one time.

8. A sample delivering method according to claim 6, wherein the sample delivering region has a length measured along the reaction lines such that a plurality of reaction tubes in each reaction line are present in the sample delivering region at one time.

* * * * *